United States Patent [19]

Imai et al.

[11] 4,388,480

[45] Jun. 14, 1983

[54] PROCESS FOR PREPARING 4-METHYL-1-PENTENE

[75] Inventors: Hirosuke Imai, Yokohama; Mitsuo Matsuno, Kawasaki; Michio Kudoh, Yokohama, all of Japan

[73] Assignee: Nippon Oil Co., Ltd., Tokyo, Japan

[21] Appl. No.: 337,775

[22] Filed: Jan. 7, 1982

[30] Foreign Application Priority Data

Jan. 27, 1981 [JP] Japan .................................. 56-9579

[51] Int. Cl.$^3$ .......................... C07C 3/02; C07C 3/20
[52] U.S. Cl. .................... 585/516; 585/510; 585/530; 252/476; 252/463
[58] Field of Search .................. 585/516, 510, 530; 252/476, 463

[56] References Cited

U.S. PATENT DOCUMENTS

| | | | |
|---|---|---|---|
| 2,986,588 | 5/1961 | Schramm | 585/516 |
| 3,175,020 | 3/1965 | Wilkes | 585/516 |
| 3,291,752 | 12/1966 | Hambling et al. | 585/516 |
| 3,305,599 | 2/1967 | Zadra et al. | 585/516 |
| 3,758,416 | 9/1973 | Furni | 585/516 |
| 3,916,019 | 10/1975 | Closson et al. | 585/516 |

FOREIGN PATENT DOCUMENTS

| | | | |
|---|---|---|---|
| 42-22474 | 11/1967 | Japan | 585/516 |
| 43-25344 | 11/1968 | Japan | 585/516 |
| 824917 | 12/1959 | United Kingdom | 585/516 |
| 1221709 | 2/1970 | United Kingdom | 585/516 |

*Primary Examiner*—Delbert E. Gantz
*Assistant Examiner*—A. Pal
*Attorney, Agent, or Firm*—Bucknam and Archer

[57] ABSTRACT

A process for preparing 4-methyl-1-pentene comprising dimerizing propylene in the presence of a catalyst, characterized in that the catalyst is composed of sodium and/or sodium amide supported on a carrier represented by the following formula $K_2O \cdot xAl_2O_3$ wherein x has a value in the range of $0.5 \leq X \leq 11$. In one embodiment, the catalyst is hydrogenated prior to the use thereof.

6 Claims, No Drawings

PROCESS FOR PREPARING 4-METHYL-1-PENTENE

This invention relates to a novel process for producing 4-methyl-1-pentene comprising dimerizing propylene. More particularly, it relates to a process for producing 4-methyl-1-pentene in a good yield and with high selectivity comprising dimerizing propylene in the presence of a catalyst composed of sodium and/or sodium amide supported on a carrier represented by the following formula $$K_2O \cdot xAl_2O_3$$

wherein x has a value in the range of $0.5 \leq x \leq 11$ or in the presence of such a catalyst previously treated with hydrogen.

4-methyl-1-pentene polymers are excellent in transparency, heat resistance, mechanical and electrical properties, and chemical resistance. In addition, polyolefins such as polyethylene or polypropylene copolymerized with 4-methyl-1-pentene exhibit improved transparency, environmental stress crack resistance and like properties. This fact indicates that 4-methyl-1-pentene is a compound which will exhibit particularly excellent capability of making such improvements when used as the comonomer as mentioned above.

It has heretofore been known that propylene is dimerized in the presence of an alkali metal such as sodium or potassium to obtain 4-methyl-1-pentene (Report by A. W. Shaw et al in J. Org. Chem. 30, 3286 (1965) for example). It has also heretofore been known to dimerize propylene in the presence of a catalyst composed of an alkali metal supported on a carrier. The known carriers so used include graphite, potassium carbonate, alkali metal silicates, alkali metal halides, magnesium sulphate and talc.

However, conventional known methods including the aforesaid ones, are disadvantageous because the yield of propylene dimer obtained by the known methods and the selectivity of 4-methyl-1-pentene attained thereby are relatively low, accompanied by the production of a large amount of by-products such as cis- and trans-4-methyl-2-pentene, 2-methyl-2-pentene, 2-methyl-1-pentene, 1-hexene, cis- and trans-2-hexene, and cis- and trans-3-hexene. They are also disadvantageous in that these by-products or isomers are close in boiling point to the desired product, 4-methyl-1-pentene, and, therefore, a high degree of fractionation is required to obtain 4-methyl-1-pentene in sufficiently high purity thereby incurring a high cost for the purification. Further, the catalysts used in the known methods will take a long time to exhibit their full catalytic activity. In other words, many of these known catalysts are slow in attaining their maximum catalytic capacity and consequently it takes a long time to allow the reaction to proceed stationarily, this rendering them inferior from the view-point of economy and stable operation. They have not only capability of catalytic dimerization but also capability of catalytic polymerization, thereby allowing the polymerization to proceed along with the dimerization. For this reason, the polymers so produced deposit on the surface of the catalyst whereby the catalytic activity regarding dimerization tends to gradually decrease. These catalysts are very often found to decrease in selectivity with a decrease in activity. These catalysts thus made less active or inactive have been solidified with resinous polymers produced as the by-products in the reactor, however, they contain yet still highly active portions remaining in the inner part thereof whereby they tend to cause their combustion and a fire by contact with the oxygen, moisture and the like in the air at the time of exchange of the used catalyst for fresh catalyst. Thus, the known catalysts are further disadvantageous in that they cannot conveniently be handled.

The present inventors made intensive studies in an attempt to eliminate the disadvantages of the known methods and catalysts and, as the result of their studies, they have accomplished this invention.

An object of this invention is to provide a process for selectively producing 4-methyl-1-pentene in a high yield.

Another object is to provide a specific catalyst usable in the process of this invention.

These and other objects will be apparent from the following description.

The objects of this invention may be achieved by dimerizing propylene in the presence of a catalyst composed of sodium and/or sodium amide supported on a carrier having a composition represented by the following formula $$K_2O \cdot xAl_2O_3$$

wherein x has a value in the range of $0.5 \leq x \leq 11$, preferably $1 \leq x \leq 5$, or in the presence of such a catalyst previously treated with hydrogen, to obtain 4-methyl-1-pentene. It has been found that this invention not only eliminates the drawbacks of the known various catalysts and methods but also enables a greater amount of sodium to be carried on a carrier so as to remarkably increase the rate of reaction and the selectivity of 4-methyl-1-pentene and allow the reaction rate and selectivity to be kept high for a long period of time.

The compounds used as the carrier in this invention and having the following chemical formula $$K_2O \cdot xAl_2O_3$$

wherein x is as defined above, may be obtained by the following method. The method comprises mixing (1) at least one potassium-containing compound such as KOH, $KOR^I$ (wherein $R^I$ is at least one member selected from $C_1$-$C_{20}$ linear or branched aliphatic hydrocarbon residues, $C_6$-$C_{30}$ aryl groups and aralkyl groups), $KHCO_3$ (hydrous or anhydrous), $K_2CO_3$ (hydrous or anhydrous), KH and $KR^{II}$ (wherein $R^{II}$ is at least one member selected from $C_1$-$C_{20}$ linear or branched aliphatic hydrocarbon residues, $C_6$-$C_{30}$ aryl groups or aralkyl groups) with (2) at least one aluminum-containing compound selected from alumina hydrates such as gibbsite, bialite, boehmite and diaspore, α- and γ-alumina, and $Al(OR^{III})_3$ (wherein $R^{III}$ is at least one member selected from $C_1$-$C_{20}$ linear or branched aliphatic, hydrocarbon residues, $C_6$-$C_{30}$ aryl and aralkyl groups), to an extent that the ratio of K/Al is x as defined above, and then reacting the resulting mixture at a temperature of usually 400°–2000° C., preferably 500°–1500° C. in the presence or absence of air, nitrogen or the like for 1–20 hours, so as to obtain the desired carrier.

The carrier so obtained is expressed herein as having $K_2O$ and $Al_2O_3$ as the components, however, this expresssion is used only for convenience's sake in indicating the composition of a carrier produced from the starting compounds (B 1) and (2) in various mixing ratios. Thus, the expression does not mean that these component compounds $K_2O$ and $Al_2O_3$ remain as such in the carrier. In truth, the carrier is mainly in the double oxide form. Therefore, compounds obtained only by mixing $K_2O$ with $Al_2O_3$ are carriers which are essentially different from those according to the present invention and will not allow a catalyst supported thereon to exhibit such high catalytic activity and high selectivity as expected with the catalyst of the present invention. There is known the following fact relating to $Al_2O_3$; more particularly, as indicated in Japanese Pat. No. 38-14706, $Al_2O_3$, particularly $\gamma$-$Al_2O_3$, will react with sodium or potassium very vigorously and the element may be carried on the $Al_2O_3$ in an amount by weight of up to about 20% thereof to obtain a comparative catalyst. The comparative catalyst so obtained is similar to the catalyst of the present invention but the former is essentially different from the latter in the respect that when the former is used in the dimerization of propylene in an attempt to obtain 4-methyl-1-pentene, the resulting dimer will mainly be 2-methyl-2-pentene or 2-methyl-1-pentene with 4-methyl-1-pentene being hardly obtained. On the other hand, as one feature of this invention, the use of the catalyst of the present invention will render it possible to obtain 4-methyl-1-pentene of at least 80% purity in a good yield. This fact proves that the carrier of the catalyst of the present invention is different from that of the comparative catalyst in which the carrier is simply a mixture of the component compounds (1) and (2).

Another feature of this invention is that a fresh catalyst according to this invention introduced into the reactor will have a very short induction period. On the contrary, the heretofore known catalysts have been found to require such an induction period of 10-15 hours at the shortest and more than a few days at the longest.

Further, in the conventional known catalysts for use in producing 4-methyl-1-pentene, the amount of sodium or potassium supported on the carrier is in the range of not more than 5 wt.%, usually about 1 to about 3 wt.% (based on the weight of the carrier). If more than 5 wt.% of sodium or potassium is attempted to be loaded on the carrier, then these alkali metals will be attached in the muddy state to the carrier whereby the resulting catalyst coagulates to form a mass which is difficult to handle industrially and the catalyst is extremely lowerd in propylene-dimerizing activity in many cases.

In contrast, the carrier used in the process of this invention and having the following formula

wherein x is as previously defined, will very rapidly adsorb and carry thereon a large amount of sodium, potassium or a hydride or amide thereof. Therefore, the carrier keeps the thus carried catalyst component satisfactorily dispersed thereby making it possible to form a catalyst which will exhibit high activity on propylene and selectivity of 4-methyl-1-pentene in the dimerization.

The catalysts according to the present invention which are excellent in dispersibility, non-coagulation, activity and selectivity and require substantially no induction period of time before the start of reaction, are very suitable for use not only in fixed bed reactors but also continuous stirred tank reactors. In the latter case, the catalysts may be introduced with propylene.

The amount of sodium and sodium amide supported on the carrier in this invention, is in the range of preferably 0.1-20 wt.% (based on the weight of the carrier) as sodium atom.

Even the catalysts of the present invention containing sodium and sodium amide in an amount of as large as 20 wt.% as sodium atom, are highly dispersible, are sufficiently reactive in the dimerization of propylene without a decrease in selectivity due to an increase in amount of the catalyst component carried, produce hardly any tars and resinous materials as the by-products and exhibit high resistance to the influence of moisture and other impurities brought into the reaction system owing to the large amount of catalyst component carried. Thus, the present catalysts may keep their activity on propylene and selectivity of 4-methyl-1-pentene at a high level for a very long period of time. It is of course clear that even the catalysts having the catalyst component carried in an amount of as small as 0.1 to 1 wt.% may be used without any trouble in the practice of this invention although they somewhat decrease in activity. In practice, an amount of 1 to 15 wt.% of the catalyst component carried is preferable.

Methods of carrying sodium on the carrier of this invention include a method of mixing under agitation sodium and the carrier in the absence of a solvent at a temperature (120°-400° C. for example) higher than the melting point of sodium, a method of depositing sodium vapor on the carrier, a method of agitating at a high speed sodium and the carrier in the presence of a high-boiling solvent such as white oil at a temperature higher than the melting point of sodium to carry the sodium on the carrier.

A usual method for carrying sodium amide on the carrier comprises immersing the carrier in an ammonia solution of sodium amide, the solution being prepared by dissolving sodium in liquid ammonia, at a temperature of usually 0°-200° C. to fully impregnate the carrier with the solution and then evaporating the ammonia from the solution-impregnated carrier to obtain a catalyst. The sodium- and/or sodium amide-containing catalyst so obtained may be treated with hydrogen at preferably 150°-400° C., at up to preferably 100 kg/cm² and for preferably 0.5-10 hours. The induction period of the resulting hydrogen treated catalyst may be further shortened.

The structure of a catalyst prepared by depositing sodium metal or sodium amide on the carrier of this invention or the structure of such a hydrogenated catalyst is not necessarily clear, but it is considered to be such that a part of the Na atoms is not only physically and chemically adsorbed on the surface of the carrier but also substituted with the atoms of the carrier.

The particle size of carrier used varies from about 0.1 mm to about 10 mm depending on the type, capacity and the like of the reactor, and it may optionally be determined within said range. Either the carriers may be baked, crushed and classified or the starting materials may be kneaded, pelletized and then baked, to obtain a carrier having the desired particle size.

The dimerization of propylene according to this invention may be effected at a temperature of 100°-250° C., preferably 140°-180° C., and at a pressure of preferably 20-200 kg/cm².

In the practice of this invention, many types of reaction are considered to be useful, among which there may be adopted, for example, batch or semi-batch type reactions using an autoclave, continuous stirred tank reactions using an autoclave into which the catalyst and propylene are continuously fed and fixed bed type continuous reactions using a reactor into which the catalyst is packed and then propylene supplied.

The amount of the catalyst used is not specifically limited in a case where an autoclave is used; however, in practice, it may preferably be in the range of 0.5–20 wt.% of propylene used. It should be noted that the amount of catalyst used is intended to mean the total weight of the carrier and sodium and/or a sodium compound each supported on the carrier.

The reaction time in the case of batch or semi-batch type reactions or the residence time in the case of continuous reactions may preferably be in the range of 1–10 hours.

The liquid hourly space velocity (LHSV) may preferably be in the range of 0.1–10 (V/V·Hr) in the fixed bed type continuous reactions.

Propylene which may be used in this invention is not necessarily highly pure; propylene which contains other olefins, diolefins, moisture, air, carbonic acid gas and the like as the impurities, may also be used if these impurities are removed by usual industrial removal methods prior to the use of the propylene. Further, it is preferable that propylene to be used contain none of saturated hydrocarbons such as ethane, propane and butane, however, propylene containing such hydrocarbons may still be used without troubles.

Any type of the aforesaid reactions of propylene may be effected in the presence of aliphatic hydrocarbons such as heptane, octane and dodecane or a mixture thereof or in the presence of any other suitable solvent which will not cause side reactions in the dimerization according to this invention.

This invention will be better understood by the following examples.

EXAMPLE 1

A catalyst No. 1 according to this invention was prepared as shown by the following reaction formulae:

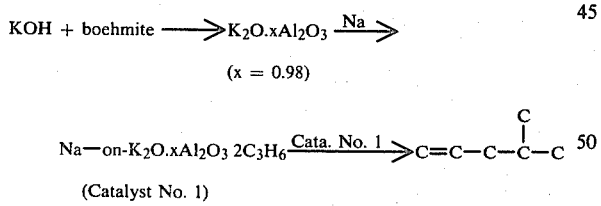

(Catalyst No. 1)

More particularly, 66 g of potassium hydroxide in the pellet form (having a water content of 15%) were pulverized, blended with 80 g of boehmite thoroughly, introduced into a crucible made of alumina, baked at 1200° C. for 5 hours in the atmosphere and then allowed to cool, after which the whole so baked was withdrawn from the crucible, placed in an alumina-made pot, pulverized by a centrifugal ball mill for two hours and then sieved to obtain a carrier portion having a particle size of finer than 60 mesh.

Sixty (60) grams of the thus obtained carrier were charged into a 300-ml three-necked flask provided with a stirrer, thermocouple and stopper for introducing sodium, heated to 150° C. in a nitrogen gas atmosphere and then incorporated with 6 g of sodium under agitation, after which the whole was heated to 200° C. and agitated at this temperature for one hour to have the sodium uniformly carried on the carrier, thereby obtaining a catalyst No. 1.

The catalyst No. 1 so obtained was used in the dimerization of propylene as detailed hereinbelow. A 100-ml stainless steel-made autoclave provided with a magnetic stirrer was charged with 16 g of the thus obtained catalyst, 100 ml of heptane as the solvent and 150 g of propylene to form a mixture which was reacted at 160° C. for 8 hours. After the end of the reaction, the autoclave was rapidly cooled to terminate the reaction thereafter and then freed from the unreacted propylene by collecting it with a trap in a dry ice-methanol bath. Further, the solvent, the reaction products and the like remaining in the autoclave reactor were recovered by distillation under a reduced pressure. The liquid so recovered was incorporated with the portion of a residue having a boiling point not lower than that of propylene dimer, the residue being the one left after the evaporation of the unreacted propylene from said trap with which it was collected, and then subjected to gas chromatography using a 50 m long glass capillary column coated with squalane thereby to find that the reactivity of the propylene was 55% and the selectivity of 4-methyl-1-pentene was 89%. Accordingly, the activity of the catalyst was 0.574 g of 4-methyl-1-pentene/g(catalyst)·hr.

EXAMPLE 2

(Refer to the reaction formula in Example 1.)

There was prepared a catalyst No. 2 composed of the same carrier as prepared in Example 1 and sodium carried on the carrier in an amount of 20 wt.% thereof. The catalyst so prepared was non-tacky and satisfactory in fluidity. Using 16 g of the thus prepared catalyst, the same reaction as in Example 1 was carried out. The analysis of the resulting reaction products showed that the reactivity of the propylene and the selectivity of 4-methyl-1-pentene were 68% and 85%, respectively. Thus, the activity of the catalyst No. 2 was 0.677 g of 4-methyl-1-pentene/g(catalyst)·hr.

EXAMPLE 3

A catalyst No. 3 according to this invention was prepared as shown in the following reaction formulae:

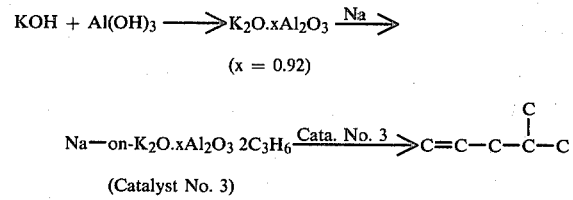

(Catalyst No. 3)

More particularly, in the same manner as Example 1, 234 g of aluminum hydroxide (produced by Wako Pure Chemical Industry Ltd.) and 180 g of potassium hydroxide (produced by the same Co.) were baked at 1200° C. for 5 hours in a muffle furnace to obtain a carrier in which the K/Al ratio was 0.92. The carrier so obtained was pulverized by the use of a centrifugal ball mill. A portion of the thus pulverized carrier, which had a particle size of finer than 60 mesh, was used in depositing sodium thereon as indicated below.

Six (6.0) grams of Na were added to 60.4 g of said pulverized carrier at 200°–220° C. by the use of the same apparatus as used in Example 1, after which the whole was agitated for 3 hours to have the Na carried on the carrier to obtain a catalyst which was indigo in color and very highly dispersible powder.

Sixteen (16.0) grams of the thus obtained catalyst were introduced into a 1000-ml autoclave in the same manner as in Example 1 and incorporated with 100 ml of heptane as the solvent and 150.8 g of propylene to form a mixture which was reacted at 175° C. for 4 hours, thereafter treated in the same manner as in Example 1 and then subjected to gas chromatography whereby it was found that the reactivity of propylene and the selectivity of 4-methyl-1-pentene were 47% and 87%, respectively. The catalytic activity was found to be 0.958 g of 4-methyl-1-pentene/g(catalyst)·hr.

EXAMPLE 4

A catalyst No. 4 according to this invention was prepared as indicated in the following reaction formulae:

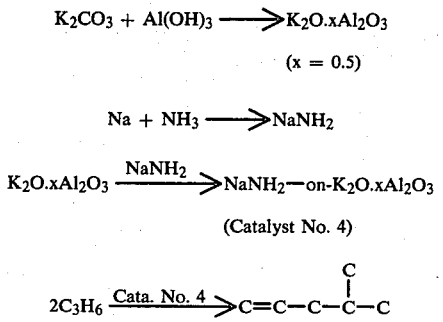

(Catalyst No. 4)

More particularly, 138.2 g of anhydrous potassium carbonate and 78.0 g of aluminum hydroxide were each pulverized to obtain particles having a particle size of finer than 16 mesh. The thus obtained particles of these two compounds were thoroughly blended together and then baked at 1200° C. for 5 hours to obtain a carrier. The thus obtained carrier was found to have a K/Al ratio of 2 by atomic absorption photoanalysis.

A stainless steel-made autoclave was charged with 15.0 g of the thus obtained carrier, 1.5 g of sodium, and 30 g of liquid ammonia to form a mixture which was agitated at room temperature for two hours, after which the ammonia and the hydrogen produced by the reaction were discharged from the mixture. The mixture so treated in the autoclave was incorporated with 100 ml of n-heptane and 150.0 g of propylene, reacted at 160° C. for 8 hours, treated in the same manner as in Example 1 and then subjected to analysis with the result that the reactivity of propylene and the selectivity of 4-methyl-1-pentene were found to be 57% and 87%, respectively. The catalytic activity was 0.564 g of 4-methyl-1-pentene/g(catalyst)·hr.

EXAMPLE 5

(Refer to the reaction formulae in Example 1.)

An autoclave was charged with 14.9 g of a 2% sodium-on-carrier catalyst prepared in the same manner as in Example 1, 100 ml of heptane as the solvent and 149 g of propylene to form a mixture which was reacted at 160° C. for 8 hours. Analysis of the reaction products showed that the reactivity of propylene and the selectivity of 4-methyl-1-pentene were 35% and 86%, respectively. The catalytic activity was 0.376 g of 4-methyl-1-pentene/g(catalyst)·hr.

EXAMPLE 6

(Refer to the reaction formulae in Example 1.)

Sixty (60) grams of potassium hydroxide and 78 g of boehmite were blended together and baked at 500° C. for 5 hours to obtain a carrier. Then, 28 g of a catalyst composed of the thus obtained carrier and sodium carried thereon in an amount of 20 wt.% thereof, and 155 g of propylene, were introduced into an autoclave and reacted at 175° C. for 4 hours. The resulting reaction products were analyzed with the result that the reactivity of propylene and the selectivity of 4-methyl-1-pentene were 75% and 80%, respectively.

The activity of the catalyst was 0.830 g of 4-methyl-1-pentene/g(catalyst)·hr.

EXAMPLE 7

A catalyst No. 7 was prepared as shown in the following reaction formulae:

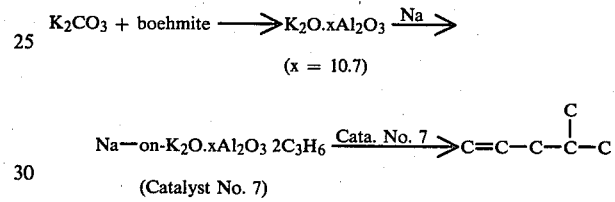

(Catalyst No. 7)

More particularly, 70 g of potassium carbonate and 660 g of boehmite were blended together and baked at 1800° C. for 7 hours to obtain a carrier in which the Al/K ratio was 10.7. It is seen from this ratio that potassium content in the thus obtained carrier was somewhat lower than that in the starting materials in mixture; the reason for this is that some of the potassium in the starting materials would have been sublimated. In addition, the X-ray diffraction graph for the thus obtained carrier did not indicate the presence of α-alumina therein.

In the same manner as in Example 1, there was prepared a catalyst composed of the thus obtained carrier and 2 wt.% of sodium carried thereon. Then, 17 g of the thus prepared catalyst were introduced into a stainless steel-made autoclave, after which 150 g of propylene were forced into the autoclave. The resulting mixture was reacted at 160° C. for 8 hours and then treated as previously mentioned. The resulting reaction products were analyzed to find that the reactivity of propylene and the selectivity of 4-methyl-1-pentene were 39.6% and 87%, respectively. The catalytic activity was 0.38.

EXAMPLE 8

(Refer to the chemical reaction formulae in Example 3).

Aluminum hydroxide and potassium hydroxide (each produced by Wako Pure Chemical Ind. Ltd.) were weighed out in the same manner as in Example 3. The whole was incorporated with a small amount of water, kneaded together, pelletized to obtain 3 mm-sized pellets and drying the thus obtained pellets at 150° C. for 15 hours. The pellets so dried were baked in a furnace at 900° C. for 8 hours to prepare a carrier. The thus prepared carrier was incorporated at 200° C. in a nitrogen atmosphere with sodium in such an amount that the sodium content in the resulting catalyst was 10 wt.% and then thoroughly blended together for two hours to obtain a catalyst No. 8.

Propylene was subjected to dimerization in the presence of the thus obtained catalyst in a reactor maintained at 160° C. and 110 kg/cm²G while introducing the propylene into the reactor at a liquid hourly space velocity (LHSV) of 1.0 hr⁻¹. The reactivity of propylene attained to a maximum of 68% three hours after the start of the reaction. The half-life of catalytic activity, that is, the time taken for the conversion of propylene to decrease from the maximum conversion to the half thereof, was 1500 hours or longer. The content of 4-methyl-1-pentene in the reaction products was 86%.

EXAMPLE 9

A catalyst No. 9 was prepared as shown in the following reaction formulae:

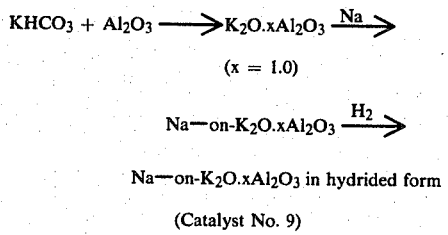

(Catalyst No. 9)

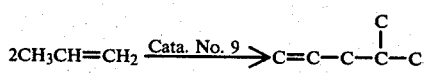

More particularly, 200 g of potassium bicarbonate and 202 g of γ-alumina were thoroughly blended together and then baked at 1000° C. for 7 hours to obtain a carrier. Then, 15 g of the thus obtained carrier were incorporated with 1.5 g of sodium and vigorously blended together at 200° C. for one hour to obtain a sodium-on-carrier.

A one-liter stainless steel-made autoclave was charged with the whole of the thus obtained sodium-on-carrier and 100 ml of n-heptane as the solvent, raised in temperature to 160° C., pressurized with hydrogen at 70 kg/cm²G and agitated for 3 hours. During this agitation, a pressure drop of 2.3 kg/cm² was appreciated. After allowing the whole to cool, it was freed from the remaining hydrogen by discharge thereof, incorporated with 150 g of propylene and reacted at 160° C. for 8 hours. The resulting reaction products were analyzed thereby to find that the reactivity of propylene and the selectivity of 4-methyl-1-pentene were 62% and 88%, respectively.

The activity was 0.620 g of 4-methyl-1-pentene/g(catalyst)·hr.

EXAMPLE 10

A catalyst No. 10 was prepared as indicated in the following reaction formulae:

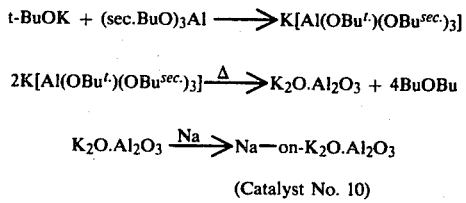

(Catalyst No. 10)

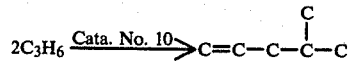

More particularly, 112 g of potassium t.butoxide and 246 g of aluminum sec.butoxide were mixed together in the presence of 200 ml of t.-butanol in a nitrogen atmosphere thereby to precipitate K[Al(OBu$^t$)(OBu$^{sec.}$)$_3$] (which was an ate-complex) as white-colored sediments. After distillation-off of the t.-butanol under a reduced pressure, the precipitate so obtained was preliminarily baked at 500° C. for 4 hours under a nitrogen stream to decompose all of the organic residues and then raised in temperature to 1200° C. and further baked at this temperature for 3 hours thereby to obtain a carrier. Then, 15 g of the thus obtained carrier were incorporated with 3 g of sodium and vigorously agitated at 200° C. for 2 hours under a nitrogen stream to obtain a catalyst No. 10.

A 1-liter stainless steel-made autoclave was charged with the whole of the thus obtained catalyst and 150 g of propylene. The whole was reacted at 155° C. for 8 hours. The analysis of the resulting reaction products showed that the reactivity and the selectivity were 49% and 91%, respectively.

The catalytic activity was 0.464.

COMPARATIVE EXAMPLE 1

Fifteen (15) grams of potassium carbonate which had been dried at 500° C. for 5 hours, were incorporated with 3 g of sodium in a nitrogen atmosphere and then vigorously agitated at 200° C. to have the sodium carried on the potassium carbonate thereby obtaining a catalyst (20 wt.% of Na carried). The thus obtained catalyst was wholly pasty at 200° C. and wholly solidified like a wax when it was cooled to room temperature.

A 1-liter stainless steel-made autoclave was charged with 16 g of the catalyst, 100 ml of n-heptane as the solvent and 150 g of propylene which was reacted at 160° C. for 8 hours in a nitrogen atmosphere. The resulting reaction products were analyzed to find that the reactivity of propylene and the selectivity of 4-methyl-1-pentene were 11% and 65%, respectively. The activity was 0.084 g of 4-methyl-1-pentene/g(catalyst)·hr. This Comparative Example 1 was effected under approximately the same conditions as Example 2, and the activity of 0.084 in this Comparative Example was clearly inferior in comparison with the activity of 0.677 in Example 2.

COMPARATIVE EXAMPLE 2

A catalyst (2 wt.% of Na carried) was prepared by having sodium carried on the same potassium carbonate as used in Comparative Example 1 in the same manner as in Comparative Example 1. The thus prepared catalyst was deep blue in color and highly dispersible. Then, 15 g of the catalyst were used in the same reaction as in Comparative Example 1, after which the resulting reaction products were analyzed to find that the reactivity of propylene and the selectivity of 4-methyl-1-pentene were 19% and 74%. In addition, the catalytic activity in this case was 0.164 which was improved as compared with Comparative Example 1 but was less than about ½ of the catalytic activity of 0.376 in Example 5 in which the dimerization was carried out under the same conditions as in this Comparative Example.

COMPARATIVE EXAMPLE 3

Potassium carbonate containing 1.0 wt.% of graphite as the binder was shaped into about 3 mm-sized pellets and dried at 200° C. for 15 hours to obtain a carrier. Then, 5 wt.% of sodium was carried on the thus obtained carrier at 200° C. in a nitrogen atmosphere to obtain a catalyst which was used in attempts to dimerize propylene in the same manner as in Example 8. The result was that it took 55 hours for the catalytic activity to reach its maximum and the reactivity at this point was 63% with the selectivity of 4-methyl-1-pentene being 74%. The half-life of the catalytic activity was 400 hours. As compared with the catalyst prepared in Example 8, the catalyst prepared in this Comparative Example was appreciated to be defective in the respects that, for example, it took a long induction period, it rapidly decreased in activity and it showed a low selectivity of 4-methyl-1-pentene.

Thus, it is clear that the catalysts wherein the carriers of this invention are used, exhibit more excellent activity than the conventional known ones even in continuous dimerization methods as mentioned above.

COMPARATIVE EXAMPLE 4

One hundred (100) grams of activated carbon and 100 g of potassium hydroxdide (having a water content of 15%) were thoroughly blended together on a ball mill and then dried at 150° C. for 5 hours to obtain a carrier. Then, 3 g of sodium were carried on 15 g of the thus obtained carrier at 150° C. in a nitrogen atmosphere to obtain a catalyst having very satisfactory dispersibility.

A 1-liter stainless steel-made autoclave was charged with 17 g of the catalyst, 100 ml of n-heptane as the solvent and 150 g of propylene to form a mixture which was reacted at 175° C. for 2 hours. The resulting reaction products were analyzed to find that the reactivity of propylene and the selectivity of 4-methyl-1-pentene were 65% and 2%, respectively.

What is claimed is:

1. A process for the preparation of 4-methyl-1-pentene which consists of dimerizing propylene at a temperature of 100° C.–250° C. in the presence of a catalyst consisting of at least one compound selected from the group consisting of sodium and sodium amide supported on a carrier of formula $$K_2O \cdot xAl_2O_3$$

wherein x has a value in the range of $0.5 \leq x \leq 11$, said carrier being prepared by heating at 400°–2000° C., a mixture of $K_2O$ or a compound capable of forming $K_2O$ and $Al_2O_3$ or a compound capable of forming $Al_2O_3$ at said temperature of 400°–2000° C.

2. A process as claimed in claim 1, wherein the catalyst is hydrogenated prior to the use thereof.

3. A process as claimed in claim 1, wherein the carrier of the formula $K_2O \cdot xAl_2O_3$ is prepared by mixing (1) at least one potassium compound, which is a member selected from the group consisting of (a) KOH and $KOR^I$ wherein $R^I$ is at least one member selected from the group consisting of $C_1$–$C_{20}$ linear or branched aliphatic hydrocarbon radicals $C_6$–$C_{30}$ aryl and aralkyl, (b) hydrous or anhydrous $KHCO_3$, hydrous or anhydrous $K_2CO_3$, (c) KH and $KR^{II}$ wherein $R^{II}$ is at least one member selected from the group consisting of $C_1$–$C_{20}$ linear or branched aliphatic hydrocarbon radicals $C_6$–$C_{30}$ aryl and aralkyl with (2) at least one aluminum-containing compound which is (a) gibbsite, bialite, boehmite, diaspore, $\alpha$- or $\gamma$-alumina, (b) $Al(OR^{III})_3$ wherein $R^{III}$ is at least one member selected from the group consisting of $C_1$–$C_{20}$ linear or branched aliphatic hydrocarbon radicals $C_6$–$C_{30}$ aryl and aralkyl, in such proportions that the ratio of K/Al is x as defined in claim 1 and then reacting the resulting mixture at a temperature of 400°–2000° C. for 1–20 hours, whereby said carrier of formula $K_2O \cdot xAl_2O_3$ is obtained.

4. The process according to claim 1 wherein the amount of sodium and sodium amide supported on said carrier is 0.1–20% as sodium atom by weight of the carrier.

5. The process according to claim 1 wherein the catalyst has been prepared by immersing said carrier in an ammonia solution of sodium amide at a temperature of 0°–200° C. until said carrier is impregnated with said solution and then evaporating the ammonia.

6. The process according to claim 1 wherein said catalyst is prepared by heating said carrier at 150°–220° C. with sodium in a nitrogen atmosphere.

* * * * *